United States Patent
Xia

(10) Patent No.: US 7,361,639 B2
(45) Date of Patent: Apr. 22, 2008

(54) GENE THERAPY AGENT FOR HAEMOPHILIA B AND ITS PREPARATION METHOD

(76) Inventor: Jiahui Xia, c/o National Lab of Medical Genetics of China, Central South University, 88 Xiangya Rd., Changsha, Hunan 410078 (CN)

( * ) Notice: Subject to any disclaimer, the term of this patent is extended or adjusted under 35 U.S.C. 154(b) by 0 days.

(21) Appl. No.: 10/362,916

(22) PCT Filed: Aug. 29, 2001

(86) PCT No.: PCT/CN01/01291

§ 371 (c)(1),
(2), (4) Date: Mar. 20, 2003

(87) PCT Pub. No.: WO02/34296

PCT Pub. Date: May 2, 2002

(65) Prior Publication Data

US 2004/0038919 A1  Feb. 26, 2004

(30) Foreign Application Priority Data

Aug. 30, 2000 (CN) .............................. 00 1 13652
Jan. 19, 2001 (CN) .............................. 01 1 02830

(51) Int. Cl.
| A01N 43/04 | (2006.01) |
| A01N 63/00 | (2006.01) |
| A01N 65/00 | (2006.01) |
| A61K 31/70 | (2006.01) |
| C12N 15/00 | (2006.01) |
| C12N 5/00 | (2006.01) |
| C12N 5/02 | (2006.01) |

(52) U.S. Cl. .................. 514/44; 435/320.1; 424/93.1; 536/23.1

(58) Field of Classification Search ................ 514/44; 424/93.1; 536/23.5; 435/320.1, 325
See application file for complete search history.

(56) References Cited

U.S. PATENT DOCUMENTS 5,935,935 A * 8/1999 Connelly et al. ............. 514/44

FOREIGN PATENT DOCUMENTS

WO    WO 00/17375    3/2000

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Walsh (2003) Gene Therapy, 10: 999-1003.*
Garret and Grisham (1995) Biochemistry, Harcourt Brace College Publishers, New York, NY., pp. 916-917.*
Yanez, et al. (1998) Gene Therapy, 5: 149-159.*

* cited by examiner

*Primary Examiner*—Joseph Woitach
*Assistant Examiner*—Robert M. Kelly
(74) *Attorney, Agent, or Firm*—Birch, Stewart, Kolasch & Birch, LLP

(57) ABSTRACT

The invention relates to site-specific integrating expression vectors for therapy Hemophilia B and to methods of preparing them. A vector of the invention contains a human Factor IX gene in a vector constructed using as a chromosome targeting sequence a polynucleotide without any important physiological function-related gene homologous to DNA on the short arms of human group D and human group G chromosomes. The vector of the invention provides high stability of Factor IX expression, high expression efficiency, no immunogenicity and safety in use.

14 Claims, 4 Drawing Sheets

SEQUENCE LISTING

<160> NUMBER OF SEQ ID NOS: 3

<210> SEQ ID NO 1
<211> LENGTH: 13928
<212> TYPE: DNA
<213> ORGANISM: Homo sapiens

<400> SEQUENCE: 1

```
gggcgaattg ggcccgacgt cgcatgctcc tctagactcg aggaattcta ccgggtaggg      60
gaggcgcttt tcccaaggca gtctggagca tgcgcttaag cagccccgct gggcacttgg     120
cgctacacaa gtggcctctg gcctcgcaca cattccacat ccaccggtag gcgccaaccg     180
gctccgttct ttggtggccc cttcgcgcca ccttctactc ctcccctagt caggaagttc     240 cccccgccc cgcagctcgc gtcgtgcagg acgtgacaaa tggaagtagc acgtctcact     300
agtctcgtgc agatggacag caccgctgag caatggaagc gggtaggcct ttggggcagc     360
ggccaatagc agctttgctc cttcgctttc tgggctcaga ggctgggaag gggtgggtcc     420
gggggcgggc tcaggggcgg gctcaggggc ggggcgggcg cccgaaggtc ctccggaggc     480
ccggcattct gacgcttcaa aagcgcacgt ctgccgcgct gttctcctct tcctcatctc     540
cggcctttcg acctgcagcg acccgcttaa cagcgtcaac agcgtgccgc agatcttggt     600
ggcgtgaaac tcccgcacct cttcggcaag cgccttgtag aagcgcgtat ggcttcgtac     660
ccctgccatc aacacgcgtc tgcgttcgac caggctgcgc gttctcgcgg ccatagcaac     720
cgacgtacgg cgttgcgccc tcgccggcag caagaagcca cggaagtccg cctggagcag     780
aaaatgccca cgctactgcg ggtttatata gacggtcctc acgggatggg gaaaaccacc     840
accacgcaac tgctggtggc cctgggttcg cgcgacgata tcgtctacgt acccgagccc     900
gatgacttac tggcaggtgc tgggggcttc cgagacaatc gcgaacatct acaccacaca     960
acaccgcctc gaccagggtg agatatcggc cggggacgcg gcggtggtaa tgacaagcgc    1020
ccagataaca atgggcatgc cttatgccgt gaccgacgcc gttctggctc ctcatatcgg    1080
gggggaggct gggagctcac atgccccgcc cccggccctc accctcatct tcgaccgcca    1140
tcccatcgcc gccctcctgt gctacccggc cgcgcgatac cttatgggca gcatgacccc    1200
ccaggccgtg ctggcgttcg tggccctcat cccgccgacc ttgccggca caaacatcgt    1260 gttgggggcc cttccggagg acagacacat cgaccgcctg gccaaacgcc agcgccccgg    1320
```

-continued

```
cgagcggctt gacctggcta tgctggccgc gattcgccgc gtttacgggc tgcttgccaa    1380
tacggtgcgg tatctgcagg gcggcgggtc gtggcgggag gattggggac agctttcggg    1440
gacggccgtg cccgcccag gtgccgagc cccagagcaa cgcgggccca cgacccata     1500 tcggggacac gttatttacc ctgtttcggg cccccgagtt gctggccccc aacggcgacc    1560
tgtacaacgt gtttgcctgg gccttggacg tcttggccaa acgcctccgt cccatgcacg    1620
tctttatcct ggattacgac caatcgcccg ccggctgccg ggacgccctg ctgcaactta    1680
cctccgggat ggtccagacc cacgtcacca ccccggctc cataccgacg atctgcgacc     1740
tggcgcgcac gtttgcccgg gagatggggg aggctaactg aaacacggaa ggagacaata    1800
ccggaaggaa cccgcgctat gacggcaata aaagacaga ataaaacgca cgggtgttgg     1860
gtcgtttgtt cataaacgcg gggttcggtc ccagggctgg cactctgtcg ataccccacc    1920 gagacccat ggggccaat acgccgcgt ttcttccttt tccccacccc accccccaag      1980
ttcgggtgaa ggcccaggc tgcagccaa cgtcggggcg gcaagccctg ccatagccac      2040
gggccccgtg ggttagggac ggggtccccc atggggaatg gtttatggtt cgtgggggtt    2100
attattttgg gcgttgcgtg gggtcaggtc cacgactgga ctgagcagac agacccatgg    2160
tttttggatg gcctgggcat ggaccgcatg tactggcgcg acacgaacac cgggcgtctg    2220
tggctgccaa acaccccga ccccaaaaa ccaccgcgcg gatttctggc gccgccggac      2280
gaactaaacc tgactacggc atctctgccc cttcttcgct ggtacgagga gcgcttttgt    2340
tttgtattgg tcaccacggc cgagtttccg cgggaccccg gccaggacct gcagaaattg    2400
atgatctatt aaacaataaa gatgtccact aaaatggaag ttttcctgt catactttgt     2460 taagaagggt gagaacagag tacctacatt ttgaatggaa ggattggagc tacggggtg     2520 ggggtgggt gggattagat aaatgcctgc tctttactga aggctcttta ctattgcttt     2580
atgataatgt ttcatagttg gatatcataa tttaaacaag caaaaccaaa ttaagggcca    2640
gctcattcct cccactcatg atctatagat ctatagatct ctcgtgggat cattgttttt    2700
ctcttgattc ccactttgtg gttctaagta ctgtggtttc caaatgtgtc agtttcatag    2760
cctgaagaac gagatcagca gcctctgttc cacatacact tcattctcag tattgttttg    2820
ccaagttcta attccatcag aagctcctta attttatacc actgacttat tttgaaggct    2880
gctataagaa acagccctat gaaactggta ttttcctact gcaaggtggc tactttaaga    2940
caattttcca ttgcattcta tcaagggatg tcttattatt atatcattat atcaagtgat    3000
gttataaata gtaagaatca gattaagggc tcatatgtcc ttctttgtat tgactgttga    3060
aaaggtatgg ggccaaattt gtagtttgtc tggaattaca tattttggg ggtctctatt     3120 atcttcatac ttatcctatc taaattttcc attgccaaat ttccttactt attttagtt     3180 ttatcctatt gctcatgtat ttttatgtct ccataagtct attttggaaa aaggcagagt    3240
actcataatt ttagtatatc ttttagcttt atgttgccat aaacctttca ttatatacat    3300
gatcaacaac agcaaattat ctcacttcag tatttagttt attattttac aaactgattt    3360
atgattgcta acatgtaact gaaggtatac actattagaa cacagttttc agtagaaagt    3420
agcactgcca ttgagtaaaa aaatgttcta acattagagc aacattctta tacaagtttg    3480
catgttgttt actgaggtct aaagcatgac tacacaaaag gctgaataaa attcagattc    3540
ttacatacac ataaaattgt tttattgaga tgacaaagta tatttattat gccacccaga    3600
atataatcca ctctgataac tgccagtgta tgcacttgct gaagtaactc agtacataaa    3660
tggtagccac aacagttgct gtgcatgaaa gttcttctct tccagattga agagtgtaca    3720
```

```
atctaaagca ttttaaaact ttaaatccct tattagctta aatataattt aaaattttag    3780
tttgccgtac ctataatttg tctgtacact aggttactaa gggtgatatg attacatatg    3840
tggatacaaa ataattttaa tggaaaatga aattagggta ctcaacaaag ataaagggta    3900
atgatcatgt acactaaccg tatttgagat tagtttaagc ctggggtagc tatacttatg    3960
tttcacagac cttgagaaga tagggaaaaa aagcttttat caacattgct aaggaacagg    4020
taaaagctaa cattaggtaa ctaagaggtg acataaaaaa gactgaataa aatatcatgg    4080
aggtttcata ataagattgg aaattccata gactaggaga gaaaagatcc caaaatatac    4140
atgctcattg ggaaaacagc tagtaagaac aaggagagat ctctatttaa tgatacaata    4200
gtagagttat aatttcctgt atattgtaaa tttcaagcat ttaaacattt tcattgaatt    4260
ataaaatatt atttgtaaaa gaaagaaaaa cagcacaact gcagattaca gatgactaag    4320
atagatgaat catgaaaagg tgctagattg tgagcggata acaatttcac acaggaaaca    4380
gctatgacca tgattacgcc aagctctcga cgggatcgcg gccgcgatcc agacatgata    4440
agatacattg atgagtttgg acaaaccaca actagaatgc agtgaaaaaa atgctttatt    4500
tgtgaaattt gtgatgctat tgcttttattt gtaaccatta taagctgcaa taaacaagtt    4560
ggggtgggcg aagaactcca gcatgagatc cccgcgctgg aggatcatcc agccggcgtc    4620
ccggaaaacg attccgaagc ccaacctttc atagaaggcg gcggtggaat cgaaatctcg    4680
tgatggcagg ttgggcgtcg cttggtcggt catttcgaac cccagagtcc cgctcagaag    4740
aactcgtcaa gaaggcgata gaaggcgatg cgctgcgaat cgggagcggc gataccgtaa    4800
agcacgagga gcggtcagc ccattcgccg ccaagctctt cagcaatatc acgggtagcc    4860
aacactatgt cctgatagcg gtccgccaca cccagccggc cacagtcgat gaatccagaa    4920
aagcggccat tttccaccat gatattcggc aagcaggcat cgccatgggt cacgacgaga    4980
tcctcgccgt cgggcatgct cgccttgagc ctggcgaaca gttcggctgg cgcgagcccc    5040
tgatgctctt cgtccagatc atcctgatcg acaagaccgg cttccatccg agtacgtgct    5100
cgctcgatgc gatgtttcgc ttggtggtcg aatgggcagg tagccggatc aagcgtatgc    5160
agccgccgca ttgcatcagc catgatggat actttctcgg caggagcaag gtgagatgac    5220
aggagatcct gccccggcac ttcgcccaat agcagccagt cccttcccgc ttcagtgaca    5280
acgtcgagca cagctgcgca aggaacgccc gtcgtggcca gccacgatag ccgcgctgcc    5340
tcgtcttgca gttcattcag ggcaccggac aggtcggtct tgacaaaaag aaccgggcgc    5400
ccctgcgctg acagccggaa cacggcggca tcagagcagc cgattgtctg ttgtgcccag    5460
tcatagccga atagcctctc cacccaagcg gccggagaac ctgcgtgcaa tccatcttgt    5520
tcaaccatgg tggatcgatc caagctccca acacaactat gtcagaagca atgtgagga    5580 gcaactgatc ctacctcacc ttatatgctc tgccctggct cctgccctct ctatcctgtg    5640
tgagcagatt ggcccttacc aaggtgtggc tctacggaat caggcttcgg tgatgacaag    5700
catatttctc cctagaatgc tgtgccactc actggcttag gagtctcagc tctgggtact    5760
ccctctgaat aatgtttgtc cttatctgtg cagagaacac tgtctctaaa gcatccttt    5820 tggcaacgca tttgctcaat caactactga attggtgtta aaattaattt tcctttttt    5880 ctcattatgc aaataagaaa ttgagaagca aagctagggg aggtcgctga gtagtgcgcg    5940
agcaaaattt aagctacaac aaggcaaggc ttgaccgaca attgcatgaa gaatctgctt    6000
agggttaggc gttttgcgct gcttcgcgat gtacgggcca gatatacgcg ttgacattga    6060
```

```
ttattgacta gttattaata gtaatcaatt acggggtcat tagttcatag cccatatatg   6120
gagttccgcg ttacataact tacggtaaat ggcccgcctg gctgaccgcc caacgacccc   6180
cgcccattga cgtcaataat gacgtatgtt cccatagtaa cgccaatagg gactttccat   6240
tgacgtcaat gggtggagta tttacggtaa actgcccact tggcagtaca tcaagtgtat   6300
catatgccaa gtacgccccc tattgacgtc aatgacggta atggcccgc ctggcattat   6360
gcccagtaca tgaccttatg ggactttcct acttggcagt acatctacgt attagtcatc   6420
gctattacca tggtgatgcg gttttggcag tacatcaatg ggcgtggata gcggtttgac   6480
tcacggggat ttccaagtct ccaccccatt gacgtcaatg ggagtttgtt ttggcaccaa   6540
aatcaacggg actttccaaa atgtcgtaac aactccgccc cattgacgca aatgggcggt   6600
aggcgtgtac ggtgggaggt ctatataagc agagctctct ggctaactag agaacccact   6660
gcttactggc ttatcgaaat taatacgact cactataggg agacccaagc tggctagcgt   6720
ttaaacgggc cctctagact cgagcggccg ccactgtgct ggatatctgc agaattccac   6780
cacactggac tagtggatcc gaccttacca ctttcacaat ctgctagcaa aggttatgca   6840
gcgcgtgaac atgatcatgg cagaatcacc aggcctcatc accatctgcc ttttaggata   6900
tctactcagt gctgaatgta cagttttct tgatcatgaa acgccaaca aaattctgaa   6960
tcggccaaag aggtataatt caggtaaatt ggaagagttt gttcaaggga accttgagag   7020
agaatgtatg gaagaaaagt gtagttttga agaagcacga gaagttttg aaaacactga   7080
aagaacaact gaattttgga agcagtatgt tgatggagat cagtgtgagt ccaatccatg   7140
tttaaatggc ggcagttgca aggatgacat taattcctat gaatgttggt gtcccttggg   7200
atttgaagga agaactgtg aattagatgt aacatgtaac attaagaatg gcagatgcga   7260
gcagttttgt aaaaatagtg ctgataacaa ggtggtttgc tcctgtactg agggatatcg   7320
acttgcagaa aaccagaagt cctgtgaacc agcagtgcca tttccatgtg aagagtttc   7380
tgtttcacaa acttctaagc tcacccgtgc tgaggctgtt tttcctgatg tggactatgt   7440
aaattctact gaagctgaaa ccattttgga taacatcact caaagcaccc aatcatttaa   7500
tgacttcact cggggttgttg gtggagaaga tgccaaacca ggtcaattcc cttggcaggt   7560
tgttttgaat ggtaaagttg atgcattctg tggaggctct atcgttaatg aaaaatggat   7620
tgtaactgct gcccactgtg ttgaaactgg tgttaaaatt acagttgtcg caggtgaaca   7680
taatattgag gagacagaac atacagagca aaagcgaaat gtgattcgaa ttattcctca   7740
ccacaactac aatgcagcta ttaataagta caaccatgac attgcccttc tggaactgga   7800
cgaacccta gtgctaaaca gctacgttac acctatttgc attgctgaca aggaatacac   7860
gaacatcttc ctcaaattg gatctggcta tgtaagtggc tggggaagag tcttccacaa   7920
agggagatca gctttagttc ttcagtacct tagagttcca cttgttgacc gagccacatg   7980
tcttcgatct acaaagttca ccatctataa caacatgttc tgtgctggct tccatgaagg   8040
aggtagagat tcatgtcaag gagatagtgg gggaccccat gttactgaag tggaagggac   8100
cagtttctta actggaatta ttagctgggg tgaagagtgt gcaatgaaag gcaaatatgg   8160
aatatatacc aaggtatccc ggtatgtcaa ctggattaag gaaaaaacaa agctcactta   8220
atgaaagatg gatttccaag gttaattcat tggaattgaa aattaacagg gcctctcact   8280
aactaatcac tttcccatct tttgttagat ttgaatatat acattctatg atcattgctt   8340
tttctcttta caggggagaa tttcatattt tacctgagct gaagcttaag tttaaaccgc   8400
tgatcagcct cgactgtgcc ttctagttgc cagccatctg ttgtttgccc ctcccccgtg   8460
```

-continued

```
ccttccttga ccctggaagg tgccactccc actgtccttt cctaataaaa tgaggaaatt    8520
gcatcgcatt gtctgagtag gtgtcattct attctggggg gtggggtggg gcaggacagc    8580
aaggggggagg attgggaaga caatagcagg catgctgggg atgcggtggg ctctatggct    8640
tctgaggcgg aaagaaccag ctggggctct aggggggtacc tagcagagat ttctatcaca    8700
cctatcaggg atacacaatt tccaagaatt cagaagtgt ttggtgttcc tattaacata     8760
aatccggaaa taacacctga gtgaactgtc ttctaattct tcaactggat ggcttttttag   8820
tgtaaaagat gttgaatact gattgacttt ttaataattt tatagtatat gtcagaaata    8880
ttgcacagtc cctatttaca tcattctaca gtggtttta aaatgtttta agaataaaaa     8940
acatgaaaac tttatttgat ttttctgagg aaataacttt ttggatttaa tttcaatgaa    9000
accgttgata acatttccct ccccaacaat ctctggcaac gatccctcag attttaatga    9060
ttatgtatta ttaccttta atacaagtag aataacactc agggaattta caacatttgt    9120
tattttcagt aaatacattg gttgaagttt aaaagtctat ccgtagtaaa cttacatctt    9180
tcaggagctt ggtcaatgtg ttctggacaa agcaggaaga tgtgactgaa atcctgaaag   9240
gagccggctc ctgcagcaca aggataatga tacatctggg tacatttctc ttcacagcat    9300
ttgatagtgg ctccaaagtg cttacaaaat gcacattgct gaaagggggta aaggagagaa  9360
atctctttat aaaaccttga aaaggaatat ttaaatataa gctgggaagg tataaaaaac    9420
tctctgtaac atcacaagta aacaaattga acctgcaaaa tattaaacaa aggattcatt   9480
aaaaataata aaatctacat tactcaattt agtgctttgt gtgctaccaa ctcatccttc    9540
cattcaaatt agaaagttag aatttcattc cttatatttt caaaaataaa ttgtgaagca   9600
ttttagaaac aaaacctaaa attttttttt aaaagcaaat agtaatatgg ttaaaggggc   9660
aggtttctat attgaggatt attataaagt tttaaatcc taccaaaact agtaatagga    9720
acatatatta tttatgagac atattactat tttttacct gcctaaaaat aaatacaaat   9780
aaattcatca attataagtt aacagggaca caaatggtta aagactcaca cacaaaaaaa   9840
acaaaactac atacttcaat gtagcaatca acttcaaatt tcttaacaaa agatggaaat   9900
gttggggaaa aaattagtca tctggtatct ttcccatttc aacctgcctc cattatcttg    9960
caagtggtaa aatgcacaga ataagcctc aaacaagagg ggcagtctag ggcaagtgaa   10020
cacataagtc ggaagaaatt atgtaaaatg ttgcatttac ttattcagtt ttcccttaga   10080
atgattcaca aactcttcct cattctccca agtccatttt gagtatcatt ttctttgaag   10140
agagtctgat gggccctgta ctatacagta tgaaatctct ctgtgggaaa tgactatcta   10200
acataaattt ttgtttacac cgttacatgg tacctacttg cttatgccat tacatgatca   10260
gtttaccttt ttctcaacct aatccaagat ccttcaattg aggcactata ctatctttgt   10320
atccaaagca ccaaaaatgc tgcttcaaac aggccctaat agataggtgt tcctatacat   10380
ataccaaaaa gacttaactt ttggtgatct tgtttgtgag tgtggctcat aaacagctta   10440
gttgagataa ctggagcctc atgtagcaga gacagttgga ccctgctaac attactgtgg   10500
atatcttcac atgttactac attgactttta tattctgcta attaaccagg gactacagta   10560
gttaaaatta taattgtttt caatgttta tgtgtaaatc tgtatctcac atactatcaa    10620
actcttcctc actgtcatca gtctactgca ttgaatccaa cataacaaag ctaaatgact  10680
cctgagggct gaatcagaaa gaagaaaaga aagagataca aaactttagt cggcccggtg   10740
gctcacacct gtaatcccag cactttggaa ggccaaggcg ggcggatcac gaggtcagga   10800
```

```
gatcgagacc atcctggctg atacagtgaa actccatctc tactgaaaat acaaaaaatt   10860
agctggacgt ggtggtgggc acctgtagtc ccagctactc aggaggctga agcaggagaa   10920
gcttctaaat aactcataaa cactaattac tgttgtgaca ctttaatttt atacaatatt   10980
tataagtata cagaataaca tttcagtgct attttggcac tcaagggtat taatgcatag   11040
cttgagtatt ctatagtgtc acctaaatag cttggcgtaa tcatggtcat agctgtttcc   11100
tgtgtgaaat tgttatccgc tcacaattcc acacaacata cgagccggaa gcataaagtg   11160
taaagcctgg ggtgcctaat gagtgagcta actcacatta attgcgttgc gctcactgcc   11220
cgctttccag tcgggaaacc tgtcgtgcca gctgcattaa tgaatcggcc aacgcgcggg   11280
gagaggcggt ttgcgtattg ggcgctcttc cgcttcctcg ctcactgact cgctgcgctc   11340
ggtcgttcgg ctgcggcgag cggtatcagc tcactcaaag gcggtaatac ggttatccac   11400
agaatcaggg gataacgcag gaaagaacat gtgagcaaaa ggccagcaaa aggccaggaa   11460
ccgtaaaaag gccgcgttgc tggcgttttt cgataggctc cgcccccctg acgagcatca   11520
caaaaatcga cgctcaagtc agaggtggcg aaacccgaca ggactataaa gataccaggc   11580
gtttccccct ggaagctccc tcgtgcgctc tcctgttccg accctgccgc ttaccggata   11640
cctgtccgcc tttctccctt cgggaagcgt ggcgctttct catagctcac gctgtaggta   11700
tctcagttcg gtgtaggtcg ttcgctccaa gctgggctgt gtgcacgaac cccccgttca   11760
gcccgaccgc tgcgccttat ccggtaacta tcgtcttgag tccaacccgg taagacacga   11820
cttatcgcca ctggcagcag ccactggtaa caggattagc agagcgaggt atgtaggcgg   11880
tgctacagag ttcttgaagt ggtggcctaa ctacggctac actagaagga cagtatttgg   11940
tatctgcgct ctgctgaagc cagttacctt cggaaaaaga gttggtagct cttgatccgg   12000
caaacaaacc accgctggta gcggtggttt ttttgtttgc aagcagcaga ttacgcgcag   12060
aaaaaaagga tctcaagaag atcctttgat cttttctacg gggtctgacg ctcagtggaa   12120
cgaaaactca cgttaaggga ttttggtcat gagattatca aaaaggatct tcacctagat   12180
ccttttaaat taaaaatgaa gttttaaatc aatctaaagt atatatgagt aaacttggtc   12240
tgacagttac caatgcttaa tcagtgaggc acctatctca gcgatctgtc tatttcgttc   12300
atccatagtt gcctgactcc ccgtcgtgta gataactacg atacgggagg gcttaccatc   12360
tggccccagt gctgcaatga taccgcgaga cccacgctca ccggctccag atttatcagc   12420
aataaaccag ccagccggaa gggccgagcg cagaagtggt cctgcaactt tatccgcctc   12480
catccagtct attaattgtt gccgggaagc tagagtaagt agttcgccag ttaatagttt   12540
gcgcaacgtt gttggcattg ctacaggcat cgtggtgtca cgctcgtcgt ttggtatggc   12600
ttcattcagc tccggttccc aacgatcaag gcgagttaca tgatccccca tgttgtgcaa   12660
aaaagcggtt agctccttcg gtcctccgat cgttgtcaga agtaagttgg ccgcagtgtt   12720
atcactcatg gttatggcag cactgcataa ttctcttact gtcatgccat ccgtaagatg   12780
cttttctgtg actggtgagt actcaaccaa gtcattctga ataccgcgcc ccggcgacc    12840
gagttgctct tgcccggcgt caatacggga taatagtgta tgacatagca gaactttaaa   12900
agtgctcatc attggaaaac gttcttcggg gcgaaaactc tcaaggatct taccgctgtt   12960
gagatccagt tcgatgtaac ccactcgtgc acccaactga tcttcagcat cttttacttt   13020
caccagcgtt tctgggtgag caaaaacagg aaggcaaaat gccgcaaaaa agggaataag   13080
ggcgacacgg aaatgttgaa tactcatact cttcctttt  caatattatt gaagcattta   13140
tcagggttat tgtctcatga gcggatacat atttgaatgt atttagaaaa ataaacaaat   13200
```

```
aggggttccg cgcacatttc cccgaaaagt gccacctgta tgcggtgtga aataccgcac    13260
agatgcgtaa ggagaaaata ccgcatcagg cgacgcgccc tgtagcggcg cattaagcgc    13320
ggcgggtgtg gtggttacgc gcagcgtgac cgctacactt gccagcgccc tagcgcccgc    13380
tcctttcgct ttcttccctt cctttctcgc cacgttcgcc ggctttcccc gtcaagctct    13440
aaatcggggg ctcccttag ggttccgatt tagagcttta cggcacctcg accgcaaaaa    13500
acttgatttg ggtgatggtt cacgtagtgg gccatcgccc tgatagacgg ttttcgccc     13560 tttgacgttg gagtccacgt tctttaatag tggactcttg ttccaaactg gaacaacact    13620
caaccctatc tcggtctatt cttttgattt ataagggatt ttgccgattt cggcctattg    13680
gttaaaaaat gagctgattt aacaaatatt taacgcgaat tttaacaaaa tattaacgtt    13740
tacaatttcc attcgccatt caggctgcgc aactgttggg aagggcgatc ggtgcgggcc    13800
tcttcgctat tacgccagct ggcgaaaggg ggatgtgctg caaggcgatt aagttgggta    13860
acgccagggt tttcccagtc acgacgttgt aaaacgacgg ccagtgaatt gtaatacgac    13920
tcactata                                                            13928

<210> SEQ ID NO 2
<211> LENGTH: 30
<212> TYPE: DNA
<213> ORGANISM: Artificial Sequence
<220> FEATURE:
<223> OTHER INFORMATION: Primer sequence TpcF

<400> SEQUENCE: 2
atgcatccta ggggaggtcg ctgagtagtg                                    30

<210> SEQ ID NO 3
<211> LENGTH: 28
<212> TYPE: DNA
<213> ORGANISM: Artificial Sequence
<220> FEATURE:
<223> OTHER INFORMATION: Primer sequence TpcR

<400> SEQUENCE: 3
atgcatccta ggtacccta gagcccag                                       28
```

GENE THERAPY AGENT FOR HAEMOPHILIA B AND ITS PREPARATION METHOD

RELATED APPLICATIONS

This application is the national phase under 35 U.S.C. § 371 of PCT International Application No. PCT/CN01/01291 which has an International filing date of Aug. 29, 2001, which designated the United States of America.

FIELD OF THE INVENTION

The invention relates to a genetic drug for treatment of hemophilia B and its preparation.

BACKGROUND OF THE INVENTION

Hemophilia B, also called second-type Hemophilia is a kind of haemorrhage. It is an X-linked, recessive hereditary disease arising due to deficiency of fibrinogen IX (FIX). Its incidence in the male is 1/30,000. Human FIX is a single-stranded glycoprotein containing 415 amino acid residues, having a molecular weight of 56 kDa. FIX can be divided into four different functional domains; in order from the N-terminus of the protein: a Gla domain (γ-carboxyl glutamic aciddomain), a growth factordomain, an activating peptide domain and a catalytic domain (or serineprotease domain). Human FIX is synthesized mainly in the liver. Its initial translation product includes a leader sequence with 46 amino acids at the N-terminus. FIX is processed into mature FIX by cleavage of the leader peptide, glycosylation and vitamin K-dependent γ-carboxylation. FIX exists in blood in as a zymogen that is activated ("FIX") by a protease activity FIXa or by the FVII-tissue factor complex. The content of FIX in plasma in normal people is 5 μg/ml and its half-life of activity is 24 hours (refer to Chuah MKL, DesireCollen & Vanden Driessche. Gene therapy for Hemophilia. J Gene Med 2001;3:3-20).

FIX is a necessary protein factor in the processes of the endogenous blood coagulation cascade response. A complex of FIX and regulatory protein accelerates the rate of the endogenous clotting cascade response thousands of times, which makes clotting process be finished just in a few minutes. Therefore, deficiency of FIX in the human body, can lead to endless spontaneous or minutely traumatic bleeding, serious joint distortion and lameness or death due to bleeding in the bowel or skull. The human FIX gene (hFIX) was identified in 1982 at chromosome Xq27.1. hFIX is composed of 8 exons, the coding sequence is 1.383 kb, encoding 415 amino acids. (Choo K H, Goule K G, Rees D J, et al. Nature 1982;299:178-180; Kurachi K, Davie E W. Proc Natl Acad Sci USA 1982;79:6461-6464.). The normal plasma concentration of FIX protein in normal plasma is 5 μg/ml (Kaufman R J. Human Gene Therapy 1999; 10:2091-2107). Clinical treatment of Hemophilia B is confined to protein substitution treatment by blood transfusion, or by administering a replenishing FIX preparation to obtain the correct plasma concentration. However, because FIX's half-life in the body is only 24 hours, patients need repeated transfusion or administration of blood preparations toremain alive. Hemophilia B patients not only undertake heavy economic burden, but also confront a threat of infection by HIV, HBV and mad cow virus.

DETAILED DESCRIPTION OF THE INVENTION

Figure 1:
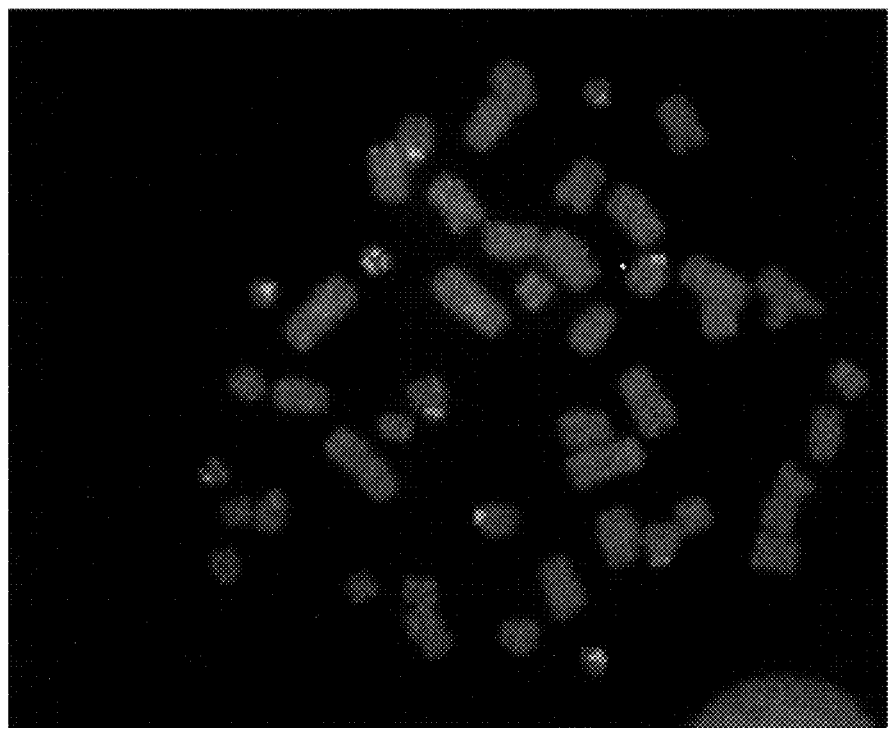
FIG. 1 shows FISH mapping of the 120 kb BMSF.

How to introduce a normal FIX gene into a patient's body to substitute the deficient FIX gene is the key problem of gene therapy for Hemophilia B. At present, vectors used for FIX gene therapy research are mainly virus vectors, such as retrovirus vectors, adenovirus vectors and adeno-associated virus vectors.

Kay et al carried out experiments of gene therapy on a dog with Hemophilia B. (refer to Kay M A, Rothenberg S, Landen C N, et al. In vivo gene therapy of hemophilia B: sustained partial correction in factor IX deficient dogs. Science 1993; 262: 117-119). The research suggests that the retrovirus (RV) transferred gene in the liver of big animals possibly has a long expression time, but the amount of expression is low. It was also found that just 0.1%-1% of liver cells of mouse are transformed by RV inexperiments performed in mice (refer to Kay M A, Li Q T, Liu J J, et al. Hepatic Gene Therapy: Persistent expression of human a 1 antitrypsin in mice after direct gene delivery in vivo. Hum Gene Ther 1992; 3:641-647). This is mainly because retroviruses do not integrate into the genome of non-dividing cells. So it is necessary to do perform partial hepatic removal to induce the remaining hepatic cells to divide when hepatic cells are used as target cells for gene therapy. Relatively low gene transfer efficiency of RV in vivo and low retransplanting efficiency of cultured cells transformed in vitro lead to low FIX expression that cannot thoroughly correct the phenotype of Hemophilia B. (refer to Lieber A. Peters M J, Gown A, et al. A modified urokinase plasminogen activator induces liver regeneration without bleeding. Hum Gene Ther 1995; 6:1029-1037; Bowles N E, Eisensmith R C, Mohuiddin R, et al. A simple and efficient method for the concentration and purification of recombinant retrovirus for increased hepatocyte transduction in vivo. Hum Gene Ther 1996; 7:1735-1742; Bosch A, McCray P B, Jr. Chang SMW, et al. Proliferation induced by keratinocyte growth factor enhances in vivo retroviral-mediated gene transfer to mouse hepatocytes. J Clin invest 1996; 98:2683-2687). Though retroviral vectors can integrate stably into the genome of target cells, retroviruses only infectdividing cells and further have the potential danger of insertional mutagenesis.

Recombinant Adeno-associated virus (rAAV) vectors are more efficient among viral vectors used for gene therapy of Hemophilia B. rAAV vectors not only express FIX cDNA s efficiently and stably in the receiving cell, but many researchers appreciate that such vectors do not contain viral genes and so are unlikely give rise to a cytotoxic T Lymphocyte response (refer to Jooss K, Yang Y, Fishe K J, et al. Transduction of dendritic cells by DNA viral vectors directs the immune response to transgene products in muscle fibers. J Virol 1998;72:4212-4223). Kay and his colleagues carried out pre-clinical research on mice and a Hemophilia B dog and clinical experiments in some patients (refer to Kay M A, Mannno C S, Ragni M V, et al. Evidence for gene transfer and expression of factor IX in Hemophilia B patients treated with an AAV vector. Nat Genet 2000; 24:257-261). Nevertheless rAAV vectors require further research for human gene therapy because of low titer, complicated preparation and poorlong-term expression. In recent years, nonviral vectors have been developed and used such as liposomes and microcapsules (refer to Hortelano G, Xu N, Vandenberg A, et al. Persistent delivery of factor IX in mice: gene therapy for Hemophilia using implantable microcapsules. Hum Gene Ther 1999;10(8);1281-1288).

In recent ten years, many effective measures in gene therapy for Hemophilia B have been taken, but no safe and stable genetic drug with one-off therapy is available. The key problem lies in that there are no safe, non immunogenic vectors that are highly efficient in transforming the target cell and and provide long expression of the therapeutic gene in the target cell.

One objective of invention is to offer a safe genetic drug for Hemophilia B therapy that provides stable expression of the therapeutic gen in a target cell.

Another objective of invention is to offer a method for preparation of the above-mentioned genetic drug.

Gene drug for Hemophilia B therapy offered by this invention contains vector-FIX recombinant whose leading sequence of objective gene is DNA sequence without important physiological function-related gene on short arm of human group D, G chromosomes or its homologous DNA sequence.

The Inventor has found two families with normal phenotype carrying additional bisatellite microchromosome (BM) that is stably inherited among two and three generations in two families, respectively, and causes no harm to a human body. The present invention is made by dissecting the BM origins and constructing a human-originated gene vector. To date, 17 such families have been reported, both in China and elsewhere, but nobody has put forward any similar idea of using BM as a gene vector.

In this study, the Inventor confirmed using the Fluorescence In Situ Hybridization technique that the BM came from the short arms of human group D chromosomes (chromosomes 13, 14 and 15) and G chromosomes (chromosomes 21 and 22), which are include abundant ribosome DNA (rDNA) that is abundant in the nucleolus organelle and that have polymorphism in length (different contents of rDNA). Gene transcription of the rDNA section during interphase of cell division is very active.

The Inventor infers that a gene in these sites will have high, stable and harmless expression if special DNA fragments isolated from BM can be used as a leader sequence of a therapeutic gene. The Inventor further infers that the therapeutic gene can be site-directed into the nucleolus organelle if sections of the short arms of human group D, G chromosomes are used in constructing a gene vector. The examples following provide proof of principle of this invention.

The inventor at first constructed a pUC19 library of BM specific DNA fragments through micro-dissection and micro-cloning techniques, from which single copy fragments from the BM and p arms of human group D and G chromosomes were selected by Southern blotting and confirmed by the FISH technique. A 120 kb specific DNA fragment (BMSF) was acquired using single copy fragments as probes to screen a human PAC genome and DNA library. The fragments also come from the BM and short arms of human group D and G chromosomes as proved by the FISH technique (FIG. 1). Analysis of the sequence of the BMSF did not identify any important physiologic function and thus it was concluded that it is safe to use the BMSF sequence as a target site for insertion of a desired DNA fragment. The Inventor further used specific DNA fragments of 120 kb or even smaller to construct a gene vector.

The Inventor considers it within the scope of the invention to use DNA sequences lacking important physiologic function-related genes on the short arm of human group D and G chromosomes or a homologous DNA sequence as a targeting sequence of a desired gene. Preferred embodiments of the gene vector target the therapeutic gene in site-directed fashion into the short arms of human group D and/or G chromosomes and the therapeutic gene can thus be expressed with high efficiency.

A "genetic drug" or "gene drug" according to the invention can also comprise reagents for assisting introduction of the therapeutic gene vector into a host cell, and especially in a site-directed fashion, such as liposomes and proteins particular to targeting the host cell. According to the targeting sequence of the therapeutic gene, different forms of vectors can be constructed by the existing technique. The methods of constructing vectors and introducing therapeutic genes into vectors are common.

On the base of obtaining a therapeutic gene leader sequence, different vectors can be constructed. The methods for constructing vectors are routine.

Figure 2:
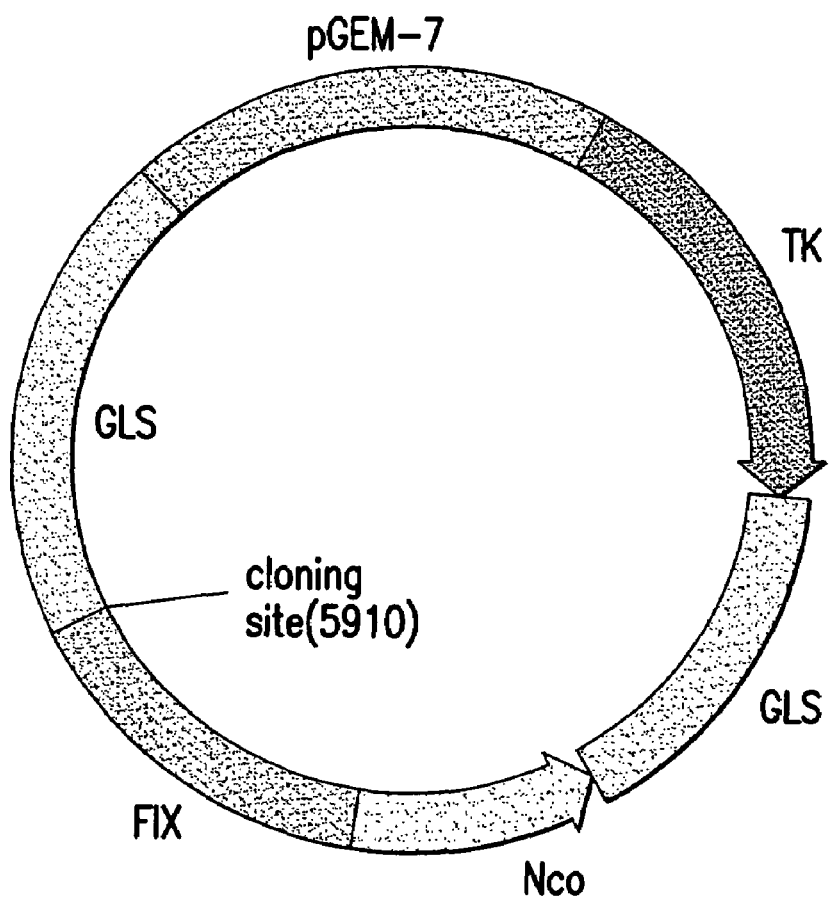
FIG. 2 shows construction of a gene vector-FIX recombinant of the invention (the whole length of gene vector sequence is 13928 bp); pGEM-7(11033-13928): vector reproductive component and prokaryotic screening system; TK (1-2840); negative screening gene for eukaryotic cells (TK promoter and TK polyA signal); Neo (4342-5910); positive screening gene for eukaryotic cells (SV40 promoter and SV40 polyA signal); FIX (5911-8677): FIX therapeutic gene (CMV promoter and BGH polyA signal); GLS(2841-4341 and 8678-11032): targeting sequence of the therapeutic gene; Cloning site (5910) for insertion of a therapeutic gene.

Example 1 provides a vector-FIX recombinant as shown in SEQ NO.1, in which a targeting sequence of 3.8 kb is obtained from BMSF. A Neo$^r$ gene for positive selection is inserted into a site at nucleotide 1500 of the leader sequence of the therapeutic gene, which is divided into two arms of 1.5 kb and 2.3 kb, respectively, using thymidine kinase (TK) as a negative screening gene. The Insertion position of the FIX therapeutic gene is at nucleotide 5910. A therapeutic gene may be inserted in either the forward or reverse direction, and the example of invention below adopts the latter. FIG. 2 is construction of vector-FIX recombinant.

The Example provides detailed description of the process of constructing an embodiment of the vector using specific DNA sequence of 3.8 kb isolated from short arms of human group D and G chromosomes as a targeting sequence of a desired gene. The vector-FIX recombinant obtained was deposited in the China Typical Culture Conservation Center (China.Wuhan Wuhan University, post code: 430072) on 29$^{th}$ of Sep., 2000, numbered: CCTCC M2000031. The deposit is named *Escherichia coli* JM109/JH/pNS FIX.

The vector carrying a therapeutic gene can be transferred into cultured human cells, such as fibroblast cells and blood stem cells, which also can be used as a gene therapy agent for treatment of hemophilia B. The Example of this invention describes an embodiment of such a delivery method using existing techniques.

In summary, to correct clinical symptoms caused by a deficient gene, cultured human cells transfected with a therapeutic gene the drug composition comprising the therapeutic gene vector can be introduced into a patient's body by means of hypodermal embed (infusion), electroporation or intravenous injection or liposome packaging and thereby the therapeutic gene can be stably expressed.

Effective Experiments of Gene Therapy:

Experiment in vitro

The recombinant human coagulatant FIX-vector was linearized and transfected into HT1080 cell by electroporation, then the positive transfected cell strain was obtained by positive and negative screening. The foreign gene integration was proved by amplifying FIX cDNA flanking an intron. The primer pair pNSNeo at the Neo gene and 876-7R at the outside of the targeting arm were used to amplify gDNA from positive transfected cells, and a 2.3 kb fragment was obtained. Sequencing analysis indicated the integration is site directed. Two positive cell strains having the FIX gene integrated into the short arms of human chromosomes 13 and 21 has fluorescence signal by FISH, which suggests site directed insertion, too. Results of assays of of FIX activity in positively transfected cultured cells reveals that activity of FIX is 3.56 μg/10⁶ cells/24 h and the cells can express stably after passaging in vitro for 449 days. Expression of the FIX product has been proven by Western blotting.

Experiment in vivo

The targeting vector of the invention is a human-source vector. There is species diversity between human beings and animals, especially for the gene drug of the invention. Were one to carry out a targeting experiment in an animal's body, it is uncertain if there is an appropriate integration site as expected and so it is improper to evaluate efficiency and stability of the vector of the invention in an animal. It is thus unnecessary to do any animal experiment in vivo.

Toxicity Evaluation of a Gene Drug

The gene drug of the invention is administered to mice via the tail vein, at 450 μg/Kg, up to 100 times as high as the single dosage of an adult by body weight. The experiment result suggests that the drug lacks toxicity and is safe when administered by intravenous injection.

The gene drug for Hemophilia B therapy offered by the invention uses DNA sequences that lack any gene having any important physiologic function and located on the p arms of human group D and G chromosomes, or its homologous DNA sequence, as a sequence to target a desired gene to a specific site. These sequences are used to construct a gene vector. Undoubtedly, the gene vector thus constructed can a therapeutic gene it contains in a site-directed manner into a special target site of the host cell. As DNA fragments of the target site do not have any important physiological function-related gene, the introduction of the therapeutic gene is safe.

In summary, because the gene therapy drug for Hemophilia B offered by the invention adopts targeting sequence of a human-source gene to construct a vector having a therapeutic gene, it has the characteristics below:

(1) Stability of expression of the therapeutic gene is good. Because the vector with the therapeutic gene can site-specifically insert the therapeutic gene into the short arms of human group D and G chromosomes, the therapeutic gene can be stably inherited with chromosomes.

Figure 3:
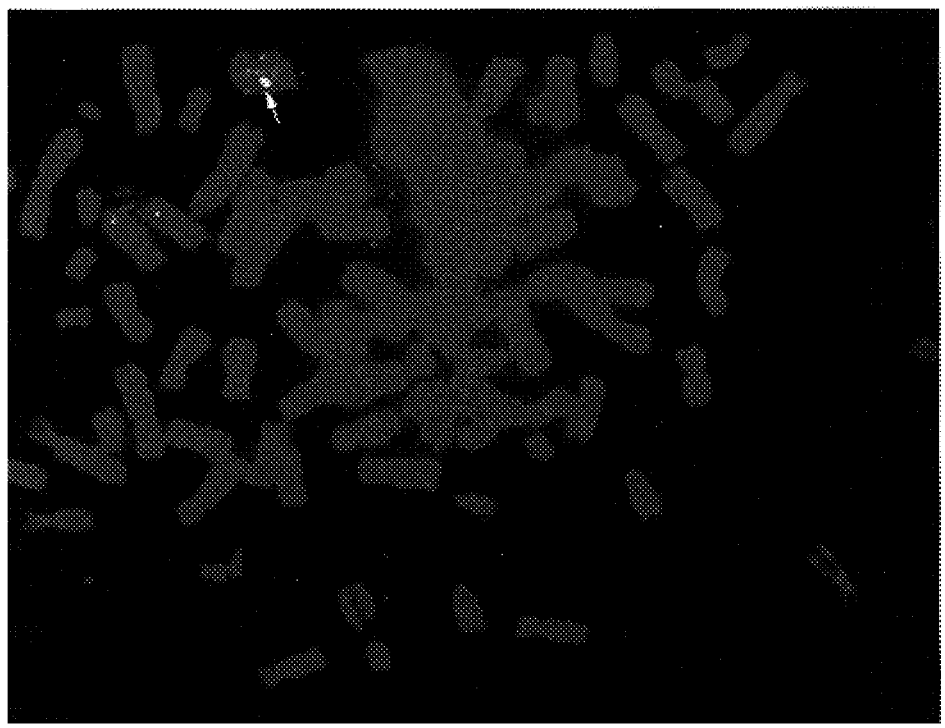
FIG. 3 shows FISH mapping of the FIX therapeutic gene in a clone of a positively transfected cell, establishes that the vector can site-direct insertion of a FIX gene into the short arms of human group D and/or G chromosomes.

(2) The security is good. The target site of the therapeutic gene does not have an important physiological function-related gene, which proves the target site is safe. Moreover, the vector can site-specifically insert a therapeutic gene into a safe target site of a cell, as has been confirmed by FISH (FIG. 3), avoiding random insertion mutation and this danger of a wild-type virus vector. Therefore expression of the therapeutic gene at the target site is safe. Though the present specification does not provide clinical cases of gene therapy, cases found by the Inventor and other researchers both in China and in other countries can prove its security from another angle.

(3) Expressive efficiency is high. First, the vector of the invention contains a targeting sequence from the short arms of human group D and/or G chromosomes, correspondingly, it has 10 target sites in a human genome with an inserting efficiency 5-10 times higher than that of other vectors. Second, the targeting sequence is from the short arms of human group D and/or G chromosomes showing active gene transcription, so the therapeutic gene introduced into the target position can be expressed with high efficiency.

(4) It has no immunogenicity. The vector is from a human source, so it will not generate immunogenicity in a human body.

The examples of the invention are only illustrative of the invention and are not to be considered limitations of the invention.

EXAMPLE ONE

The Preparation of Gene Targeting Sequence

Obtaining a Clone of Gene Leading Sequence-PAC 1.1 BM specific pUC19 library constructed by micro-dissection, PCR and microclone methods (see, Deng H X, Yoshiura K, Dirks R W, et al. Hum Genet 1992, 89:13).

1.2 Obtaining and Identifying of BM Specific pUC19

(1) Preparation of Bacterial Colony Matrix Membrane

Draw 14×14 squares on two nylon membranes marked with A or B signal, and place the two membranes into two dishes containing solid LB medium, respectively, and pick at random 14×12 white colonies from the library dishes and put it into the relevant wells, including 100 ng single-copy DNA as a positive control in row 13, 100 ng gDNA as a negative control in row 14. Then the two dishes are incubated at 37° C. for 10-12 hrs. After taking the membrane out of the dishes, conserve B membrane at 4° C. and treat the A membrane on a filter soaked with the following solution and procedure, 10% SDS, 5 min; 0.5N NaOH/1.5M NaCl, 3 min; 1.5 M NaCl/0.5M Tris.HCl, 3 min; 2×SSC/0.2 M Tris.HCl, 10 min; vacuum dry at 80° C. for 2 hrs and then conserve it for use at 37° C.

(2) Preparation of gDNA Probe

Sample 50-75 ng of gDNA, make up in ddH2O to 11 ml and boil at 100° C. for 10 min to denature, and perform a random primer labeling reaction following the recipe below.

| | |
|---|---|
| 2 m M d NTP (d ATP-), | 3 μl, |
| primer mixtture, | 2 μl |
| Klenow enzyme, | 1 μl |
| α-³² P-d ATP, | 3 μl | vortex the mixture and incubate at 37° C. for 30 min. Add 8 μl stop mixture to the system and pass it through a G-50 column to purify the probe.

(3) Hybridization

The membrane is soaked in 2×SSC solution for 10 min, then slightly wiped to remove the colony pieces on the surface of membrane. Then pre-hybridize in 5 ml hybridization buffer for 30 min. According to the value of liquid scintillation counting, sample the probe solution in the proportion of 1.2×10⁶ cpm/ml hybridization buffer and boil at 100° C. for 10 min to denature, and then add 5 ml fresh hybridization buffer to hybridize with the colony matrix membrane at 65° C. for 12 hrs. Wash the membrane as follows: 2×SSC/0.1% SDS, at room temperature for 10 min; 2×SSC/0.1% SDS, 65° C. for 10 min; 0.1×SSC/0.1% SDS, 65° C. for 10 min, autoradiograph at −70° C. If the signal of hybridization has no or only a slight signal, it is considered as a signal of a single copy.

(4) Sequence and Identification by Southern Blotting

Pick the clone on the Membrane B without hybridization signals to amplify at small scale and then extract plasmid DNA for sequencing. Compared to data of Genbank; it is a single copy if the sequences have no similarity. Finally, digest the plasmid with EcoRI and separate the insert DNA and label it with α-³²P-dATP by the random primer method, and hybridize with the gDNA digested with EcoRI enzyme on the nylon membrane using the methods described above, one or two bands of hybridization indicate the detected DNA is single copy.

1.3 Obtaining and Identifying the Specific PAC Clone of BM and Chromosomal Short Arm of Group D and/or G (1) Obtaining of Positive Clone Number by Scanning Human PAC gDNA Library Label the 260 bp single copy probe P8-7 by random primer method with α-$^{32}$P-d ATP; purify using a G-50 column (medium size); conserve at 4° C. for use; soak 7 pieces of membranes with 2×SSC buffer for 10 min; pre-hybridize at 55° C. for 3 hrs; denature the probe at 100° C. for 10 min; hybridize with PAC membrane by adding 50 ml hybridization buffer at the proportion of 4.6×10$^5$ cpm/ml; wash membrane: 2×SSC, RT for 10 min once, 2×SSC/0.1% SDS 65° C. 10 min twice; autoradiograph at −70° C. for 12 hrs; develop X-ray film; read the positive clone number following the introduction.

(2) Pick the Positive Clone Number at Random on the 5 Different Plates and Buy PAC Clone 1.4 PAC DNA hybridized with the metaphase cells is confirmed as coming from short arm of chromosomes of Group D and/or G by FISH (see FIG. 1).

The methods for doing so can be found in J. Sambrook et al. Molecular Colony. Second Edition. Cold Spring Harbor Laboratory Press. 1989

2. Obtaining a Gene Targeting Sequence DNA

Main materials, β-agarase (Bio-Labs), Not I restriction enzyme, Agarose (1) Digested PAC169 with Not I enzyme
(2) Separate the insert DNA (about 120 kb in size) by PFGE method
Pulse electrophoresis conditions:
Electrode buffer: 0.5× TBE, High strength Analytical Grade Agarose (Bio-Rad, Low Melting point Agarose LMP) 1%,
Switch Time: 2 sec - - - 15 sec.
Electrophoresis Time: 18 hrs,
voltage: 6 V/cm,
Angle: 120°,
Temperature: 14° C.
(3) Stain with ethidium bromide (EB) solution (0.2 μg/ml) for 30 min after electrophoresis and cut out the 3.8 kb (120 kb) gel band according to a molecular weight marker with a sterile knife.
(4) Digest the gel with β-agarase and precipitate the DNA with alcohol

EXAMPLE TWO

Preparation of a recombinant gene vector-FIX gene drug for hemophilia B.

1. construction of gene vector and transduction of therapeutic gene 1.1 construction of the gene vector 1.1.1 Digest PAC DNA with Nsi I and Stu I (blunt end) enzymes, recover the 3.8 kb DNA fragment with normal agarose gel and purification by electroelution.

1.1.2 Digest pGEM-TK vector DNA with Hind III enzyme and fill-in the ends to blunt with Klenow enzyme and yield blunt ends.

1.1.3 Further digest the product of Hind III repair with NsiI enzyme.

1.1.4 Ligate the purified 3.8 kb/Nsi I+Stu I enzyme product and the product digested with HK+Nsi I at 16° C. for 17 hrs.

1.1.5 Transform *E. coli* JM109 with the ligation product, and culture in a petri dish on Amp+ medium at 37° C. for 18 hrs.

1.1.6 Pick the single copy clone at random and double enzyme-cut with HindIII+Nsi I enzymes and identify the positive clone.

1.1.7 Ligate Neo/Xba I+Nhe I and pGEM-TK-3.8 KB/Nhe I to construct pNS2 gene vector.

1.2 The transduction of FIX gene 1.2.1 Clone FIX gene (CDS) into pcDNA 3.1(−)

1.2.2 Design TPCF and TPCR primers and amplify FIX gene and expression component (CMV promoter and BGH poly A signal) to load the two ends with AvrIII enzyme digestion sites; the sequence of primer is TpcF: ATgCAT<u>CCTA</u>ggggAggTCgCTgAgTAgTg (SEQ ID NO: 2)
Avr II
TpcR; ATgCAT<u>CCTA</u>ggTACCCCTAgAgCCCAg (SEQ ID NO: 3)
Avr II 1.2.3 Digest the FIX gene with Avr II enzyme and ligate it's the expression components (CMV promoter and BGH polyA signal) to the pNS2 vector digested with Nhe I enzyme.

1.2.4 The ligated product was transformed into JM109 *E. coli*, and the recombinant strain (Collection number is CCTCC M200031) was obtained.

Methods for the above steps may be found in J. Sambrook et al. MolecularCloning. Second Edition. Cold Spring Harbor Laboratory Press. 1989

2. Extraction of gene vector DNA 2.1 Materials:
2.1.1 QIAGE Plasmid Maxi Kit
2.1.2 Medium: liquid LB
Tryptone 5 g
Yeast extract 2.5 g
NaCl 2.5 g
ddH$_2$O adjust the volume to 500 ml
Autoclave
2.1.3 Ampicillin: 100 mg/ml (=1000×)
2.2 Methods
1) Pick a single positive clone into 3 ml LB medium (Amp+), incubate at 37° C. at 250 rpm for 1 hr.
2) Add 100 μl primary culture to 100 ml LB medium (Amp+), incubate at 37° C. at 250 rpm for 16 hrs.
3) Centrifuge at 600 g rotor speed for 15 min at 4° C. to obtain a pellet.
4) Resuspend the pellet with 10 ml Buffer P1.
5) Add 10 ml Buffer P2 and invert slightly 6 times for 5 min at room temperature.
6) Add 10 ml pre-cooled Buffer P3, invert slightly 6 times on ice for 20 min.
7) Centrifuge at 20000 g at 4° C. for 30 min.
8) Quickly transfer supernatant to a 40 ml of high-speed centrifugation tube and centrifuge at 20000 g at ° C. for 15 min.
9) Equilibrate a QUIAGEN Tip 500 column with 15 ml Buffer QBT.
10) Filter the supernatant through the QUIAGEN Tip 500.
11) Wash the column with 15 ml Buffer QC.
12) Elute with Buffer QF and collect the elution solution.
13) Add 10.7 ml (0.7× volume) isopropanol to elution solution and mix up.
14) Centrifuge at 15000 g at 4° C. for 30 min
15) Dispose of the supernatant and add 5 ml 70% ethanol and centrifuge at 4° C., 15000 g for 10 min to wash DNA precipitation.
16) Dispose of the ethanol and air-dry the DNA for 10 min, and then dissolve the DNA precipitate with TE buffer.
The recombinant of gene vector-FIX has been deposited in the Chinese Type culture Collection Center (Wuhan University, China, postcode: 430072) on 29th of Sep., 2000. The deposit number is CCTCC M200031. The name is *Escherichia coli* JM109/JH-4/PNS-FIX.

EXAMPLE THREE

The recombinant of gene vector-FIX of Example 2, comprising a FIX gene, was transduced into HT1080 host cells and expressed. The transformed HT1080 cells were preserved in the Chinese Type Culture Collection Center (Wuhan University, China, postcode: 430072) on the 18th of Aug., 2000. The deposit number is CCTCC M20005. The cell strain is named human fibrosarcoma cell strain/JH-1/FIX.

1. MATERIAL
   1.1 Cell: HT1080
      Medium; high sugar DMEM+10% FBS (HT1080), EMEM+10% FBS
   1.2 Electroporation device: Bio-Rad Company
2. Methods
   1) Culture the cells in a 75 cm² culture bottle and grow up to 70%-80% confluence.
   2) Harvest the cells and wash twice with HeBs buffer and count the number of cells.
   3) Centrifuge at 15000 rpm at 4° C. for 10 min.
   4) Resuspend the cells with appropriate amount of HeBs buffer to a cell concentration of $10^6$-$10^7$ cells/ml.
   5) Add 0.8 ml cell supernatant and 10 ug DNA vector together into a 4.0 ml cuvette.
   6) Electric shock at 260V voltage, 550 μF capacitance for 11-13 msec.
   7) Transfer electric shocked cells into 75 cm² culture bottle and add 14 ml culture medium with double antibiotics and culture at 37° C., 5% $CO_2$ for 24-48 hrs.
   8) Add G418 to a final concentration of 300 μg/ml to select positively transfected cells, change medium each 2-3 days and add G418 again, using normal cells as a control.
   9) Count living clone numbers in the transfected cell cultures when all of the normal cells die in seven days, and change the amount of G418 to 150 ug/ml to maintain the culture.
   10) Continue to screen transfected cells with final concentration 500 ng/ml G418.
   11) Assay expression activities of the transferred gene when most of the cells die and add 250 μg/ml G418 to maintain the culture.
3. Result Transfect the vector to transfer FIX gene to HT1080 cells with electroporation method and attain the positive cell strain after positive and negative screening, the site-directed insertion of gene is confirmed by FISH (see FIG. 3).

Figure 4:
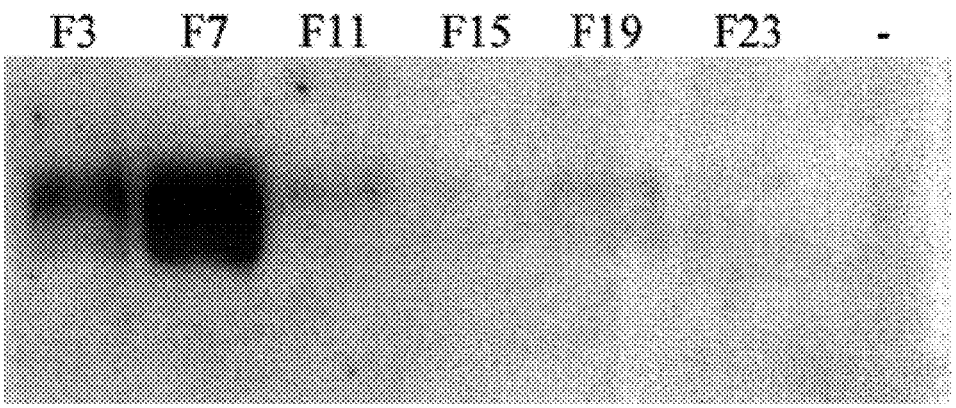
FIG. 4 shows the result of Western blotting of samples from positively transformed cells. F3-F23 are 6 different positive cell strains, "−" denotes negative control.

Activities of FIX gene increase from 0.1 ug/ml to 4.27 μg/ml compared to negative control. Furthermore, the amount of FIX expression is still 3.15 μg/ml after 144 days (see Table 1). The products of FIX expression are confirmed by Western Blotting (see FIG. 4).

TABLE 1

Activity detection of FIX gene (μg/$10^6$ cells/24 hr)

| Days after transformation | clone F23 |
| --- | --- |
| 35 | 4.27 |
| 72 | 4.39 |
| 100 | 4.6 |
| 111 | 3.95 |
| 139 | 4.0 |
| 144 | 3.15 |
| 449 | 3.56 |

The Certification of Safety

1. The Case of Safety in Population of People

The Inventor has been engaged in research on human and medical genetics since 1973; he found and identified 732 karyotypes which were found in the world submitted by 470 clinical cytogenetists in 189 labs around China. Among these karyotypes there are 41 karyotypes which involve short arms of Group D and/or G chromosomes. No matter how the fragment translocated to short arms of Group D and/or G chromosomes originated from which chromosome of chromosome 1-22, or what different lengths of fragment from the same chromosome containing one to thousands of genes, the phenotypes of carriers themselves are normal. This finding indicates that genes translocated to chromosomal short arm in Groups D and G can be expressed normally. Therefore, it is thought safe to use the short arm of Group D, G chromosomes as a target site of gene therapy.

1. Karyotype: 46,XX,t(1;12;22;15;11;8) (1qter→1p11::8p23→8pter;12pter→12q11::1p11→1pter; 22qter→22p11::12q11→12qter;15pter→22p11→22pter; 11pter→11q21::15q15→15qter;8qter→8p23::11q21→11qter)
   phenotype: female, 28 years old, normal phenotype carrier
   material provider: Wu subing, Cytogenetics laboratory, Department of gynecology and obstetrics, first affiliated hospital of Zhongshan Medical University, Guangzhou 2. Karyotype: 46,XY,t(1;13) (1pter→1q32::13p11→13qter→13p11::1p32→1qter).
   Phenotype: female, 24 years old, normal phenotype carrier
   Material provider: Xiao Chen, Department of biology, Harbin Medical University, Harbin 150086

3. Karyotype: 46, XX, t(2;15) (2pter→cen→15qter; 2qter→cen→15pter)
   phenotype: female, 26 years old, normal phenotype carrier
   material provider: Guo Yuping, et al. Cytogenetics Department, Jiangxi provincial gynecology and obstetrics hospital, Nanchang 330006, Jiangxi province 4. Karyotype: 46,XY,t(2;21) (2pter→cen→21pter; 2qter→cen→21qter)
   phenotype: male, 32 years old, normal phenotype carrier
   material provider: Kang Guoqing, et al. Department of genetics, the second affiliated hospital of Shangxi Medical College, Taiyuan 030001

5. Karyotype: 46,XY,t(3;21) (2qter→cen→22pter; 3qter→cen→22qter)
   phenotype: male, 26 years old, normal phenotype carrier
   material provider: Gao Yun, Department of toxicology, Bingzhou municipal Medical College, Bingzhou 256603, Shangdong province 6. Karyotype: 46,XY,t(3;22) (3pter→cen→22pter; 3qter→cen→22qter)
   phenotype: male, 29 years old, normal phenotype carrier
   material provider: Shi Huajin. Department of genetics, Jingzhou Women and Baby hospital, Jingzhou 121000, Liaoning province 7. Karyotype: 46,XX,t(4;15) (4pter→4p13::15p13→15pter; 15qter→15p13::4p13→4pqter)
   phenotype: female, 28 years old, normal phenotype carrier
   material provider: Zhou Ling, et al. Laboratory of genetics, the Wuhan Children hospital, Wuhan 430016, Hupei province 8. Karyotype: 46,XY,t(4;21) (4pter→4p15::21p11→21 pter; 21qter→21p11::4p15→4pqter)
   phenotype: female, 25 years old, normal phenotype carrier material provider: Xu Jinfang, et al. Laboratory of genetics, the sixth people's hospital of Shanghai, Shanghai 200000
9. Karyotype: 46,XY,t(4;14) (4qter→4-q31::14p11→14pter; 14qter→14p11::4q31→4qter)
phenotype: male, normal phenotype carrier
material provider: Zhou Mingjun, et al. Xuchang Municipal Central Hospital, Xuchang 161000, Henan province
10. Karyotype: 46,XY,t(4;14) (4qter→4q35::14p11→14pter;14qter→14p11::4q35→4qter)
phenotype: male, 27 years old, normal phenotype carrier
material provider: Zhang Xiuquan, et al. Hushan Municipal Women and Nursling Hospital, Hushan 528000, Guangdong province
11. Karyotype: 46,XX,t(6;22) (5qter→5q13::22p11→22pter; 22qter→22p11::5q13→5qter)
phenotype: female, 32 years old, normal phenotype carrier
material provider: Zhao Jianping, Anyang Municipal Women and Nursling Hospital, Anyang 455000, Henan province
12. Karyotype: 46,XY,t(6;22) (6pter→cen6→22qter; 6qter→cen22→22pter)
phenotype: male, 25 years old, normal phenotype carrier
material provider: Zhu Xinxia, et al. Laboratory of cytogenetics, Department of Gynecology and Obstetrics, Number 88 Hospital, Taian 271000, Shangdong province
13. Karyotype: 46,XY,t(6;22) (6qter→6p21::22p11.2→22pter; 22qter→22p11.2::6q21→6pter)
phenotype: male, 33 years old, normal phenotype carrier
material provider: Yang Qinglan, Department of Gynecology and Obstetrics, affiliated hospital of Bingzhou Medical College, Bingzhou 256603, Shangdong province
14. Karyotype: 45,XX,t(7;21) (7qter→7p22::21p12→21qter)
phenotype: female, 23 years old, normal phenotype carrier
material provider: Sun Qingji, et al. Laboratory of genetics, the Wuhan Children hospital, Wuhan 430016, Hubei province
15. Karyotype: 46,XY/46XX,t(7;14) (7pter→7q11::14p11→14pter;14qter→14p11:7q11→7qter)
phenotype: male, 28 years old, normal phenotype carrier
material provider: Li Luyun, Xia Jiahui, et al. State Key Laboratory of Medical genetics (Human Medical University), Changsha 410078, Hunan province
16. Karyotype: 46,XY,t(8;14) (8pter→8p21::14p12→14pter;14qter→14p12::8p13→8pter)
phenotype: male, 27 years old, normal phenotype carrier
material provider: Shi Huajin, et al. Department of genetics, Jingzhou Women and Baby hospital, Jingzhou 121000, Liaoning province
17. Karyotype: 46,XY,t(9;14) (9pter→cen→14pter; 9qter→cen→14qter)
phenotype: male, 28 years old, normal phenotype carrier
material provider: Cheng Qiuyun, et al. Department of reproduction medicine, first affiliate hospital of Hengyang medical college, Hengyang 421001, Hunan province
18. Karyotype: 46,XY,t(9;22) (9pter→9p13::22p12→22pter;22qter→22p12::9p13→9pter)mat
phenotype: female, 31 years old, her mother, a young sister of her, a young brother of her and her son have the same phenotype as her, that is normal phenotype carrier
material provider: Li Luyun, Xia Jiahui, et al. State Key Laboratory of Medical genetics (Hunan Medical University), Changsha 410078, Hunan province
19. Karyotype: 46,XX,t(9;14) (9pter→9q12::14p12→14pter; 14qter→14p12::9q12→9qter).
Phenotype: female, 32 years old, normal phenotype carrier
Material provider: Sun Yanyang, et al, Department of biology, Harbin Medical University, Harbin 150086
20. Karyotype: 46,XX,t(9;15) (9pter→9q21::15p12→15pter; 15qter→15p12::9q21→9qter)mat.
Phenotype: female, 36 years old, normal phenotype carrier
material provider: Zhu Guizhen, et al. Laboratory of cytogenetics, Department of Gynecology and Obstetrics, Number 88 Hospital, Taian 271000, Shangdong province
21. Karyotype: 46,XX,t(10;13) (10pter→10q24::13p11→13pter; 13qter→13p11::10q24→10qter)
Phenotype: female, 28 years old, normal phenotype carrier
Material provider: Yan Dunqing, Department of Gynecology and Obstetrics, affiliated hospital of Qingdao Medical College, Qingdao 266003, Shangdong province
22. Karyotype: 46,XX,t(10;13) (10pter→10q24::13p12→13pter; 13qter→13p12::10q24→10qter)
Phenotype: female, 29 years old, normal phenotype carrier
Material provider: Zhang Yinru, et al. Department of neurology First affiliated hospital of Zhongshan Medical University, Guangzhou 510080, Guangdong province
23. Karyotype: 46,XX,t(11;14) (11pter→cen→11qter→cen→14qter)
material provider: Wang Zhiyong, Department of genetics, Zhacheng County people's hospital, Zhacheng County 476200, Henan province
24. Karyotype: 46,XX,t(11;21) (11pter→11p11::21p11→21pter; 21qter→21p11::11p11→11pter)
Phenotype: female, 26 years old, normal phenotype carrier
material provider: Zheng Jun, et al. Department of genetics, Shanxi provincial women and nursling hospital, Xian 710003 Shanxi province
25. Karyotype: 46,XX,t(11;15) (11pter→11q13::15p12→15pter; 15qter→15p12::11q13→11qter)
Phenotype: male, 23 years old, normal phenotype carrier
material provider: Yang Ruifang, et al. Medical center of Obstetrics, affiliated hospital of Shandong Medical University, Jinan 250012, Shandong province
26. Karyotype: 46,XX,t(12;14) (12pter→cen→14pter::12qter→cen→14qter)
Phenotype: female, 28 years old, normal phenotype carrier
material provider: Han Weitian, et al. Department of eugenics, Liaoning provincial institue of family planing, Shenyang 110031, Liaoning province
27. Karyotype: 46,XX,t(13;16) (13pter→13p11::16p11.2→16pter;16qter→16p11.2::13p11→13pter
Phenotype: female, 27 years old, normal phenotype carrier
material provider: An Songlan. Department of genetics, Dalian municipal gynecology and obstetrics, Dalian 110078, Liaoning province
28. Karyotype: 46,XY/46,XX,t(13;13) (13qter→13p12:; 13p12→13qter)

Phenotype: male, 39 years old, normal phenotype carrier
material provider: Li Luyun, Xia Jiahui, et al. State Key Laboratory of Medical genetics (Hunan Medical University), Changsha 410078, Hunan province 29. Karyotype: 46,XY,t(14;18) (14pter→cen→18pter; 14qter→cen→18qter)
Phenotype: male, 30 years old, normal phenotype carrier
material provider: Wang Sugui, et al. Beijing Institute of family planing technology guidance, Beijing 100006

30. Karyotype: 46,XX,t(14;15) (14pter→14q13:: 15p13→15pter; 15qter→15p13::14q13→14qter)
Phenotype: female, 28 years old, normal phenotype carrier
material provider: Li Luyun, Xia Jiahui, et al. State Key Laboratory of Medical genetics (Hunan Medical University), Changsha 410078, Hunan province 31. Karyotype: 46,XX,t(15qter→cen→22qter)
Phenotype: female, 27 years old, normal phenotype carrier
material provider: Li Luyun, Xia Jiahui, et al. State Key Laboratory of Medical genetics (Hunan Medical University), Changsha 410078, Hunan province 32. Karyotype: 46,XY,t(15;18) (15pter→cen=18pter; 15qter→cen→18qter)
Phenotype: male, 30 years old, normal phenotype carrier
material provider: Ren Guoqing, et al. Beijing Institute of family planing technology guidance, Beijing 100006

33. Karyotype: 46,XX,t(15;20) (15pter→cen→2pter; 15qter→cen→2qter)
Phenotype: female, 26 years old, normal phenotype carrier
material provider: Wang Xin, et al. Laboratory of genetics, department of obstetrics, the second affiliated hospital, Hunan Medical University, Changsha 410011, Hunan province 34. Karyotype: 46,XX,t(15;22) (15pter→15p11:: 22p13→22pter;22qter→22p13::15q11→15qter)
Phenotype: female, 27 years old, normal phenotype carrier
material provider: Hu Shengdi, Department of genetics, Hainan provincial people's hospital, Haikou570011, Hainan province 35. Karyotype: 46,XX,t(15;22) (15pter→15q22:: 22p11→22pter;22qter→22p11::15q22→qter)
Phenotype: female, 29 years old, normal phenotype carrier
material provider: Li Murou, Department of genetics, Xinjiang Medical College, Urumchi 830054

36. Karyotype: 46,XY,t(16;21) (16pter→16q11:: 21p11→21pter;21qter→22p11::16q12→16qter)
Phenotype: male, 29 years old, normal phenotype carrier
material provider: Zhang Huifang, et al, Institute of family planing technology of Guangdong, Guangzhou510080, Guangdong province 37. Karyotype: 46,XX,t(18;21) (18pter→cen→21pter; 18qter→cen→21qter)
Phenotype: female, normal phenotype carrier
material provider: Shi Huajin, et al. Laboratory of genetics, Jingzhou women and nursling hospital, Jingzhou 121000, Liaoning province 38. Karyotype: 46,XX,t(18;21) (18pter→18q11:: 21p12→21pter;21qter→22p12::18q11→18qter)
Phenotype: female, 26 years old, normal phenotype carrier
material provider: Li Xiulin, et al, laboratory of genetics, department of pediatrics, first affiliated hospital of Chinese medical university, Shenyang 110011, Liaoning province 39. Karyotype: 45,X,dic(Y;13) (Ypter→Yp1200:: 13p11→cen→13qter)
Phenotype: male, 4 years old, normal phenotype carrier
material provider: Xia Jiahui, et al. State Key Laboratory of Medical genetics (Hunan Medical University), Changsha 410078, Hunan province 40. Karyotype: 46,XY,t(Y;15) (15pter→15p12:: Yq12→Ypter)pat.
Phenotype: male, 4 years old, normal phenotype carrier
material provider: Xia Jiahui, et al. State Key Laboratory of Medical genetics (Hunan Medical University), Changsha 410078, Hunan province Abnormal chromosome carriers above showed no abnormal syndrome, which explains that not only nucleolus tissue can receive foreign genes but also allows foreign genes to express normally.

2. Toxicity Test

Acute Toxicity Studies of Gene Drug of the Invention

The objective of this study is to investigate the acute toxicity reaction and the conditions of death upon intravenous injection of a gene drug provided by this invention.

Materials:

(1) Animals

Kunming strain mice (n=40); body weight 20.4±1.1 g, the number of female and male is equal. All of the experimental animals and feeds were provided by the Experimental Animal Department of Xiangya Medical School, Central South University. The mice are of eligible certification of medical experiment animals issued by the administrative committee of Hunan provincial medical experiment animals.

2 Drugs

Gene drugs were prepared as provided in this invention. The sterile water is made up to 11.25 μg/ml injection before experiment.

Method

Pretest: Among 10 little white mice, the number of female and male mice is equal. The gene drug was injected into the mice by the tail vein. The dose of gene drug for mice in pretest was 450 μg/kg (100 times high as that for adults). No toxicity appeared.

Formal experiment: According to the characteristics of the gene therapy drug, an experiment was conducted using the pretest dosage. The experimental animals were divided into two groups: test and control groups. The mice were given 450 μg/kg gene drug for test group (equal to 100 times of clinical dose for human being by body weight). The mice in control group were given by the tail vein the equal volume of distilled water (0.4 ml/10 g, each time). The reaction of the animal to the drug was observed after injection, continuous observation of 14 days, urine and stool situations of animals, common activity and death number were recorded. All of the animal were dissected and the conditions of the thoraxand abdominal cavity were observed by the end of day 14.

Results

The experiment on mice acute toxicity: The control groups mice (n=20) exhibited no abnormal activity or death through continuous observing over 14 days. The mice appear weary and immobile within 30 minutes after two injections, and subsequently resume normalactivity. Over 14 days continuous observation, no abnormality was observed in the animals' food uptake, urine and stool, or common activity. No animals died. There is no significant difference between the test group and control group through pathological examination. The results are shown in Table 2.

TABLE 2 human gene vector FIX acute toxicity test results

| Group | n | concentration (μg/ml) | vein injection (ml/10 g/once) | times to clinical dose | death number | general condition |
|---|---|---|---|---|---|---|
| control | 20 | | 0.4 | | 0 | normal |
| FIX | 20 | 11.25 | 0.4 | 100 | 0 | normal |

CONCLUSION

The vein injection dosage of mice human gene vector FIX (equal to 100 times of clinical dose according to body weight calculation) caused no deaths. No obvious acute toxicity was indicated and the gene drug appears safe for intravenous injection administration and suitable for clinical application.

The invention claimed is:

1. A plasmid vector comprising:
   a) a marker gene providing for selection for the vector in a mammalian host cell;
   b) a polynucleotide segment comprising nucleotides 2841-4341 of SEQ ID NO: 1;
   c) a polynucleotide segment comprising nucleotides 8678-11032 of SEQ ID NO: 1;
   d) a polynucleotide segment providing for replication of the vector in a bacterial host cell; and
   e) a polynucleotide segment providing for selection for the vector in a bacterial host cell.

2. The plasmid vector of claim 1 further comprising an expression cassette comprising a polynucleotide encoding Factor IX inserted between components b) and c).

3. The plasmid vector of claim 2, in which the expression cassette comprising a polynucleotide encoding Factor IX has the sequence of nucleotides 5911-8677 of SEQ ID NO: 1.

4. A method for site-directed insertion of a Factor IX encoding DNA segment into the short arm of human chromosome 13, 14, 15, 21 or 22 comprising transforming a human cell in vitro with the plasmid vector of claim 3.

5. A method for site-directed insertion of a Factor IX encoding DNA segment into a short arm of human chromosome 13, 14, 15, 21 or 22 comprising transforming a human cell in vitro with the plasmid vector of claim 2.

6. A method for expressing Factor IX comprising:
   transforming human cells in vitro with the vector of claim 2,
   selecting cells that express Factor IX.

7. The plasmid vector of claim 1 further comprising an expression cassette comprising a polynucleotide encoding Factor IX inserted between components b) and c).

8. The plasmid vector of claim 7, in which the expression cassette comprising a polynucleotide encoding Factor IX has the sequence of nucleotides 5911-8677 of SEQ ID NO: 1.

9. A method for site-directed insertion of a Factor IX encoding DNA segment into the short arm of human chromosome 13, 14, 15, 21 or 22 comprising transforming a human cell in vitro with the plasmid vector of claim 8.

10. A method for site-directed isertion of a Factor IX encoding DNA segment into the short arm of human chromosome 13, 14, 15, 21 or 22 comprising transforming a human cell in vitro with the plasmid vector of claim 7.

11. A method for site-directed insertion of a desired DNA segment into the short arm of human chromosome 13, 14, 15, 21 or 22 comprising transforming a cell comprising said human chromosome 13, 14, 15, 21 or 22 in vitro with the plasmid vector of claim 1.

12. The vector deposited as CCTCC M2000031.

13. A method for making a vector comprising:
   i) isolating a DNA fragment of human genomic DNA from a short arm of a group D,G chromosome comprising nucleotides 2841-4341 of SEQ ID NO: 1;
   ii) isolating a DNA fragment of human genomic DNA from a short arm of a group D or group G chromosome comprising nucleotides 8678-11032 of SEQ ID NO:1; and
   iii) inserting the DNA fragments into a vector comprising a gene encoding a selectable marker effective in a mammalian cell.

14. The method of claim 13, in which the vector comprising a gene encoding a selectable marker effective in a mammalian cell further comprises a polynucleotide segment providing for replication of the vector in a bacterial host cell and a polynucleotide segment providing for selection for the vector in a bacterial host cell.

* * * * *